United States Patent [19]

Basset et al.

[11] 4,080,398

[45] Mar. 21, 1978

[54] PROCESS FOR PREPARING CATALYSTS FOR USE IN OLEFINS CONVERSION REACTIONS

[75] Inventors: Jean-Marie Basset, Caluire; Jacques Bousquet, Irigny; Robert Mutin, Lyon, all of France

[73] Assignee: Entreprise de Recherches et D'Activites Petrolieres (ERAP), Paris, France

[21] Appl. No.: 772,319

[22] Filed: Feb. 25, 1977

Related U.S. Application Data

[62] Division of Ser. No. 558,558, Mar. 14, 1975, abandoned.

[30] Foreign Application Priority Data

Mar. 15, 1974  France .................................. 74 08844

[51] Int. Cl.$^2$ ................................................ C07C 3/62
[52] U.S. Cl. ................................................. 260/683 D
[58] Field of Search ..................... 260/683 D; 558/558

[56] References Cited

U.S. PATENT DOCUMENTS

| 3,268,618 | 8/1966 | Fletcher et al. | 260/683.15 R |
| 3,530,196 | 9/1970 | Singleton | 260/683 D |
| 3,536,777 | 10/1970 | Alkema et al. | 260/683 D |
| 3,544,647 | 12/1970 | Pennella | 260/683 D |
| 3,634,539 | 1/1972 | Alkema et al. | 260/683 D |
| 3,686,136 | 8/1972 | Doyle | 260/683 D |
| 3,778,385 | 12/1973 | Zuech | 260/683 D |

FOREIGN PATENT DOCUMENTS

| 1,106,016 | 3/1968 | United Kingdom | 260/683 D |

*Primary Examiner*—Delbert E. Gantz
*Assistant Examiner*—C. E. Spresser
*Attorney, Agent, or Firm*—Burgess, Ryan and Wayne

[57] ABSTRACT

There is disclosed a process for the metathesis of olefins. The process utilizes as a catalyst an alumina carrier which is treated with a chlorination agent with the subsequent addition to tungsten compounds, molybdenum compounds or mixtures thereof to the chlorinated carrier.

16 Claims, No Drawings

PROCESS FOR PREPARING CATALYSTS FOR USE IN OLEFINS CONVERSION REACTIONS

This is a division of application Ser. No. 558,558, filed Mar. 14, 1975, now abandoned.

This invention concerns a new process for preparing metallic catalysts containing tungsten and/or molybdenum, supported on a carrier.

Such catalysts are mainly used in olefin conversion reactions, such as the dismutation of acyclic olefins or the polymerization of cyclic olefins.

These reactions are also known as olefin disproportion, disproportionation or matathesis. They comply with the following general reaction formula:

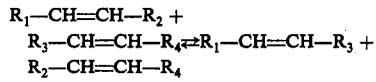

$$R_3—CH=CH—R_4 \rightleftarrows R_1—CH=CH—R_3 + R_2—CH=CH—R_4$$

where the radicals $R_1$, $R_2$, $R_3$ and $R_4$ represent identical or different hydrocarbon chains, saturated or unsaturated and optionally possessing functional groups. The radicals $R_1$ and $R_2$ of an olefin may also belong to the same chain (cyclic olefin).

In general, the disproportion consists of converting the olefins in the mixture into other olefins with larger and smaller numbers of carbon atoms per molecule than in the original mixture.

Tungsten or molybdenum catalysts are generally used in such reactions, in combination with various co-catalysts. Many publications have dealt with such catalytic systems, including British Pat. Specification No. 1,266,340. The disproportion process described in this patent involves a catalyst consisting of:
- a tungsten or molybdenum salt (chloride);
- an organo-metallic compound, such as $C_2H_5AlCl_2$;
- a solid carrier such as alumina, silica, or silica-alumina.

The catalyst is also activated by an initiator, containing a hydroxyl or thiol group. This patent illustrates the superiority of the supported heterogeneous catalyst over the non-supported homogeneous catalyst.

Furthermore U.S. Pat. No. 3,637,893 discloses a method in which matathesis is obtained by bringing a molybdenum or tungsten oxide, supported on a solid refractory inorganic oxide, into contact with a perchlorinated hydrocarbon. Preparation of the catalyst accordingly consists of chlorinating simultaneously the carrier, usually alumina, and the tungsten or molybdenum metallic oxide combined with it.

Finally, U.S. Pat. No. 3,476,728 discloses the use in cyclopentene polymerization of a catalyst obtained by reaction between a mixture of tungsten chloride and aluminium chloride and an organo-metallic compound of halogenated aluminium. Polymerization is activated by the addition of a peroxy organic compound.

The present invention relates to a novel process for preparing tungsten and molybdenum catalysts, basically comprising a carrier and a tungsten and/or molybdenum compound. Such catalysts are particularly useful in disproportionation reactions.

These new catalysts avoid the use of organo-alumina compounds of the type $R_{3-x}AlCl_x$, which are very expensive. Activating agents also become unnecessary.

Finally, this new catalytic system is extremely flexible in practical uses, and can be used in the form of a solid catalyst in suspension in the reactive liquid (slurry), offering the combined advantages of homogeneous catalysis (high turn-overs) and heterogeneous catalysis (simplicity), or in the form of a heterogeneous catalyst, with the solvent-removed.

The catalyst is prepared in two stages: first, a carrier comprising alumina, is treated with a chlorination agent, in the gaseous phase at a temperature of between 25° and 400° C, and second, the tungsten and/or molybdenum compound is added to the carrier.

The carrier contains more than 25%, and preferably more than 50%, by weight of alumina. Any type of alumina may be used (Y, δ, n, etc.). However, it is preferable to use an alumina with large specific surface-area, 10 to 800 m²/g, preferably 50 to 600 m²/g and, still more preferably, 300 to 500 m²/g.

During the first stage, chlorination can be performed by any chlorination agent which is effective in the gaseous phase. This agent must contain, together with the chlorine element, at least one metalloid from Groups III to VI of the periodic table of elements, or a transition metal, since such metalloids and transition metals all produce stable oxides. Chlorination agents include, without being confined to, compounds with the following formulae:

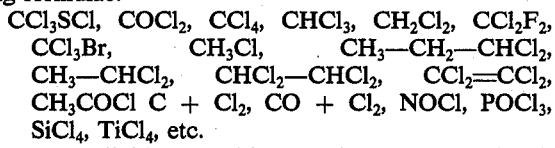

The metalloid or transition metal needs not be chemically connected to chlorine: $C + Cl_2$, for example. The stable oxides that result are of the type $CO_2$, $SO_2$, $NO_2$, $P_2O_5$, $SiO_2$, $TiO_2$, etc.

Chlorination should be performed under non-reducing conditions, for instance in the presence of a non-reducing gas such as nitrogen, argon, carbon dioxide or an oxygenated gas such as air. If a reducing gas is present, hydrochloric acid gas forms, deactivating the carrier.

A suitable chlorination agent is carbon tetrachloride($CCl_4$), but this is only because it is cheap and easy to use.

Chlorination should also be performed at a temperature of between 25° and 400° C. Temperature should be prevented from rising too much, to prevent the formation of free aluminium trichloride. For this reason, the recommended temperature is between 250° and 350° C.

The amount of chlorine added to the carrier should be equivalent to 1 to 20% of the weight of carrier, the exact quantity depending on the specific surface-area of the initial carrier and the chlorination temperature. It has been found that the maximum number of chlorine ions ($Cl^-$) that can be fixed to the surface of an alumina carrier is usually between 5 and 12 per 100 Å².

Although catalysts will be active even with fairly small quantities of chlorine fixed to the carrier, the level of activity will be much greater in carriers with high chlorine content.

The chlorine compound should be added to the carrier fairly slowly, to ensure uniform chlorination, and prevent the temperature from raising due to the exothermic nature of the reactive mixture.

The duration of chlorination can vary, depending on the temperature, but is usually between 1 mn and 50 hours. If the temperature is high enough, around 350° C, only a few minutes will be needed, while several hours halogenation may be necessary at temperatures of around 200° C.

During the second stage, the tungsten and/or molybdenum compound is added to the carrier chlorinated during the first stage.

Suitable tungsten and molybdenum compounds are salts such as tungsten hexachloride and molybdenum pentachloride, and carbonyl complexes such as $W(CO)_5PO_3$ and $Mo(CO)_6$.

The quantity of metallic compound added to the carrier is such that the tungsten and/or molybdenum metal is equivalent to 0.1 to 30% of the weight of catalyst.

The amount of tungsten and molybdenum compounds added to the carrier depends on the surface-area of the carrier material. The ratio $$\frac{\text{weight of } W \text{ (or } Mo) \text{ in the tungsten complex}}{\text{weight of carrier}}$$

should be between 1 and 20%, with an optimum of 10% for alumina with a specific surface-area of 300 m$^2$/g.

The molybdenum and tungsten compound can be added to the alumina support by any normal method, such as dry mixing, impregnation, or ion exchange. If is often not necessary to impregnate the carrier with the tungsten or molybdenum compound, since when it is dissolved it often soaks into the chlorinated carrier, which thereupon turns a typical yellowish-red colour.

The catalyst can even be prepared in situ, in which case the chlorinated carrier and dissolved tungsten or molybdenum compound are placed in the reaction zone with the reagents. This does not affect catalysis.

One variant on the process consists of subjecting the alumina support to heat treatment before chlorination, in order to check the satisfactory hydration of the alumina and ensure that chlorination will take place satisfactorily. This preliminary heat treatment is carried out at a temperature of above 100° C. To ensure full effectiveness, temperature should be above 200° C, but while there is no theoretical upper limit, it should not be allowed to exceed 800° C, to prevent serious reduction in the specific surface-area of the carrier. The treatment can be performed either in a flow of gas, such as nitrogen, hydrogen or oxygen, or in a vacuum. If hydrogen is used, however, nitrogen should be blown through afterwards.

In another variant of the process, the initial carrier can be treated with a platinum salt, such as $H_2PtCl_6$, so that after reduction in hydrogen at approximately 500° C, the carrier contains 0.1 to 1% by weight of Pt.

This new carrier, treated in the way described above, produces a catalytic system with three functions:
  metathesis of olefins;
  hydrogenation of olefins;
  hydroisomerization of the saturated hydrocarbons obtained; while ensuring the elimination of any coke precursors that form on the surface of the catalyst.

The examples below illustrate the process for preparing these new catalysts, and also their use in olefin reactions, particularly olefin metathesis. More specifically, they are designed to show the specific advantages of by this new process, particularly the advantage of chlorinating the carrier before adding the active metal, compared with the method of chlorinating both carrier and active substance. Olefin metathesis is performed at low temperatures, between −20° and +150° C.

In these examples, the degree of activity of the catalyst is reflected in the initial rate of the reaction, expressed in moles per liter per minute (mole $\times$ l$^{-1}$ $\times$ min$^{-1}$).

EXAMPLE 1

This example, given for comparison, concerns an unchlorinated catalyst, and does not come within the field of the present invention.

500 mg $\gamma$-alumina with a specific surface-area of 300 m$^2$/g was activated in a vacuum at 500° C for 15 hours. The resulting solid (A) was vacuum-sealed in situ, in a glass container.

Cis-2-pentene metathesis was performed in a batch-type apparatus, the various reagents being placed in it in the following order:
  500 mg solid A
  26.6 $\times$ 10$^{-5}$ moles complex $W(CO)_5P_3$
  60 ml chlorobenzene as solvent
  27.3 $\times$ 10$^{-3}$ moles cis-2-pentene.

When argon had been blown through the apparatus carefully, the container of solid A was broken. Analysis of the gaseous phase, in relation to time, showed the progress of reaction at 25° C, and thereby initial reaction rate.

The rate was 8 $\times$ 10$^{-6}$ moles $\times$ l$^{-1}$ $\times$ min$^{-1}$.

EXAMPLE 2

This example shows the increase in rate compared with example 1, following chlorination of the solid.

500 mg $\gamma$-alumina with a specific surface-area of 300 m$^2$/g was activated in a vacuum at 500° C for 15 hours. The resulting solid was placed in contact at 30 torr with carbon tetrachloride at 350° C for 1 hour, then vacuum-sealed in a glass container (solid B).

Metathesis of cis-2-pentene was performed, with the following ingredients:
  500 mg solid B
  26.6 $\times$ 10$^{-5}$ moles complex $W(CO)_5P0_3$
  60 ml chlorobenzene as solvent
  27.3 $\times$ 10$^{-3}$ moles cis-2-pentene.

The reaction temperature was 25° C.

Argon was blow through the apparatus, after which the container of solid B was broken; the solid immediately turned red, the metathesis began.

Initial rate was 800 times greater than for example 1: 6.5 $\times$ 10$^{-3}$ moles $\times$ l$^{-1}$ $\times$ min$^{-1}$.

EXAMPLE 3

This example illustrates the difference between activating the solid with $CCl_4$ and depositing $AlCl_3$ on an alumina, in which case preliminary treatment with HCl is required, to prevent hydrolysis of the $AlCl_3$ by the OH groups in the alumina.

500 mg $\gamma$ alumina was activated by heat treatment in a vacuum at 500° C for 15 hours, then placed in contact at 700 torr with gaseous hydrochloric acid at 200° C for 15 hours. $AlCl_3$ was placed in a vacuum at the same temperature for 5 hours, and sublimated on the solid at approximately 350° C. The catalyst was then vacuum-sealed (solid C), and used in metathesis in the same way as in example 1 and 2. Catalytic activity was low, with only 0.03% conversion after 240 minutes' reaction. The initial rate, of 2.6 $\times$ 10$^{-7}$ moles $\times$ l$^{-1}$ $\times$ min$^{-1}$ was very low, as compared to the highly active solid in example 2.

EXAMPLE 4

Examples 5 and 5 illustrate the possibility of selecting various precursor aluminae before chlorination.

500 mg P oxide alumina (Degussa) with a specific surface-area of 90 m$^2$/g was vacuum-treated at 500° C for 15 hours, then chlorinated in the same way as in example 2. The solid was then tested as a co-catalyst of W(CO)$_5$P0$_3$, under exactly the same conditions as in example 2. The catalyst proved highly active at 25° C, and thermodynamic balance was achieved in 44 minutes. The initial rate, $3.3 \times 10^{-3}$ moles $\times$ l$^{-1} \times$ min$^{-1}$, was however lower than that found with a γ alumina.

EXAMPLE 5

500 mg η-alumina with a specific surface-area of 330 m$^2$/g was treated and chlorinated in the same way as in example 2. Metathesis of cis-2-pentene was then performed under the same conditions as in example 2. The catalyst proved highly active, with 48% conversion in 18 minutes. The initial speed of $6.5 \times 10^{-3}$ moles $\times$ l$^{-1} \times$ min$^{-1}$ was similar to that obtained with γ-alumina.

EXAMPLE 6

This example illustrates the possibility of using various tungsten-derived compounds with varying degrees of oxidation, and with chlorinated alumina as co-catalyst.

500 mg η-alumina was chlorinated in the same way as in example 2. Metathesis of cis-2-pentene was performed as follows.

Sample of chlorinated alumina in container:
$1.47 \times 10^{-3}$ moles WCl$_6$ purified by vacuum sublimation 60 ml hexane
$27.6 \times 10^{-3}$ moles cis-2-pentene were placed in a static reactor, at a temperature of 25° C.

After 4 minutes' reaction, the system was active in the metathesis, and the initial rate was $3.5 \times 10^{-4}$ moles $\times$ l$^{-1} \times$ min$^{-1}$.

EXAMPLE 7

This example illustrates the use of another metal than tungsten in the catalytic complex used with the chlorinated alumina.

500 mg η-alumina was chlorinated in the same way as in example 2. Metathesis was then performed, using the following ingredients:
sample of chlorinated alumina:
$27 \times 10^{-5}$ moles Mo(CO)$_6$
60 ml hexane
$27.6 \times 10^{-3}$ moles cis-2-pentene.

Conversion after 4 minutes' reaction was 1%, and the initial rate was $5.4 \times 10^{-4}$ moles $\times$ l$^{-1} \times$ min$^{-1}$.

EXAMPLE 8

This example relates to the use of another activating carrier than chlorinated alumina, namely chlorinated TiO$_2$, which also possesses high Lewis acid properties.

To begin with, 500 mg Degussa titanium oxide was treated in O$_2$ at 400° C for 20 hours. After being placed in a vacuum at 200° C, this solid was brought into contact at 80 torrs with CCl$_4$ at 100° C for 4 hours, then vacuum-sealed.

Metathesis was then performed in the same way as in example 2, except that chlorinated TiO$_2$ was used as a co-catalyst. Activity at 25° C proved very low, with only 1.6% conversion after 92 hours' reaction, and with an initial rate of $6 \times 10^{-7}$ moles $\times$ l$^{-1} \times$ min$^{-1}$.

EXAMPLE 9

Examples 9 and 10 illustrates the difference between the present process and the process described in U.S. Pat. No. 3,637,893, which consists of treating a molybdenum or tungsten oxide deposited on silica-alumina, and possibly alumina, with perchlorinated hydrocarbons.

500 mg η alumina with 10% molybdenum, expressed in MoO$_3$, was treated in oxygen at 550° C for 20 hours, then with CCl$_4$ at 350° C for 20 hours. The resulting solid was vacuum-sealed in a glass container. Metathesis of cis-2-pentene was performed, using the following ingredients:
500 mg chlorinated catalyst
60 ml chlorobenzene
$28.6 \times 10^{-3}$ moles cis-2-pentene (olefin $^{Mo}$ = 100).
Reaction temperature was 25° C.

The catalyst showed low activity during metathesis, and the initial rate was only $5.5 \times 10^{-9}$ moles $\times$ l$^{-1} \times$ min$^{-2}$.

EXAMPLE 10

The same operation was performed, using WO$_3$/Al$_2$O$_3$.

500 mg WO$_3$/Al$_2$O$_3$ with 10% W, expressed as WO$_3$, was treated at 550° C in oxygen for 20 hours, then chlorinated with CCl$_4$ at 350° C for 20 hours. The resulting solid was used in olefin metathesis, with the following ingredients:
500 mg chlorinated catalyst
60 ml C$_6$H$_5$Cl
$26.10^{-3}$ moles cis-2-pentene ((olefin/W)= 100 molar).

The catalyst was less active than catalysts described in the present invention.

The initial rate was $5.7 \times 10^{-6}$ moles $\times$ l$^{-1} \times$ min$^{-1}$.

EXAMPLE 11

This example illustrates the heterogeneous catalysis nature of the present invention. In this case, metathesis was performed in cross-bed dynamic microreactor. The catalyst was prepared as follows.

200 mg η alumina was activated at 400° C in nitrogen for 10 hours. The temperature was then lowered to 200° C, and CCl$_4$ added to the catalyst at 30 torrs, in a flow of nitrogen, for 16 hours. The catalyst was then blown through with dry nitrogen for 1 day at the same temperature.

A sufficient quantity of W(CO)$_5$P0$_3$, equivalent to 5% of the weight of initial η-alumina, was dissolved in 10 ml anhydrous benzene, and this was added in a flow of nitrogen to the reactor containing the chlorinated alumina. The benzene was then evaporated by blowing nitrogen through at 50° C for 16 hours.

This catalyst was used in the metathesis of cis-2-pentene at 50° C. The reagent pressure was 1 torr and the flow-rate of vector gas 1 liter/hr. After 17 minutes' reaction, thermodynamic balance was achieved, showing very high catalytic activity.

What is claimed is:

1. In a process for the metathesis of olefins wherein olefins are contacted with a catalyst the improvement which comprises utilizing as said catalyst a composition prepared by the method which comprises:

(1) treating a solid inorganic oxide carrier comprising alumina substantially free of molecular water with a chlorination agent in the gaseous phase at a temperature of between 25° C and 400° C under non-reducing conditions to form a chlorinated carrier; and then (2) adding to said chlorinated carrier a composition selected from the group consisting of tungsten compounds, molybdenum compounds or mixtures thereof;

(3) said chlorination agent being a compound containing chlorine and at least one metalloid selected from Groups III to VI of the periodic table of the elements, or a transition metal.

2. The process of claim 1 wherein said olefins are contacted with the catalyst at a temperature between −20° and +150° C.

3. The process of claim 1 in which said carrier contains more than 50% by weight of alumina, with a specific surface area of between 10 and 800m$^2$/g.

4. The method of claim 1 wherein said solid inorganic oxide carrier is treated with said chlorination agent for between 1 minute and 50 hours.

5. The process of claim 1 wherein about 1 – 20% by weight of chlorine is added to the inorganic oxide carrier during the treatment with the chlorination agent.

6. The process of claim 1 wherein between 0.1 and 30% by weight, calculated as tungsten metal, of said tungsten compound is added to the inorganic oxide carrier after treatment with said chlorination agent.

7. The process of claim 1 wherein 0.1 – 30% by weight, calculated as molybdenum metal, of said molybdenum compound is added to the inorganic oxide carrier after treatment with said chlorination agent.

8. The process of claim 1 wherein the solid inorganic oxide carrier is heat treated at a temperature of between 100° and 800° C to form a carrier substantially free of molecular water.

9. The process of claim 1 wherein said solid inorganic oxide carrier contains from about 0.1 – 1% by weight of platinum before treatment with the chlorination agent.

10. The method of claim 1 wherein said tungsten compounds, molybdenum compounds or mixtures thereof are added to said chlorinated carrier under substantially anhydrous conditions.

11. The process of claim 1 wherein said chlorination agent is a member selected from the group consisting of $CCl_3SCl$, $COCl_2$, $CCl_4$, $CHCl_3$, $CH_2Cl_2$, $CCl_2F_2$, $CCl_3Br$, $CH_3Cl$, $CH_3—CH_2—CHCl_2$, $CH_3—CHCl_2$, $CHCl_2—CHCl_2$, $CCl_2=CCl_2$, $CH_3COCl$, $C + Cl_2$, $CO + Cl_2$, $NOCl$, $POCl_3$, $SiCl_4$, and $TiCl_4$.

12. The process of claim 11 wherein said chlorination agent is a member selected from the group consisting of $CCl_3SCl$, $COCl_2$, $CCl_4$, $CHCl_3$, $CHCl_2$, $CCl_2F_2$, $CCl_3Br$, and $CH_3Cl$.

13. The process of claim 12 wherein said chlorinating agent is carbon tetrachloride.

14. The process of claim 1 wherein said tungsten compound is tungsten hexachloride or its corresponding carbonyl complex.

15. The process of claim 1 wherein said molybdenum compound is molybdenum pentachloride or its corresponding carbonyl complex.

16. The process of claim 1 wherein said solid inorganic oxide carrier is treated with said chlorination agent at a temperature between 250° and 350° C.

* * * * *

UNITED STATES PATENT OFFICE
CERTIFICATE OF CORRECTION

Patent No. 4,080,398     Dated March 21, 1978

Inventor(s) Jean-Marie Basset, et al

It is certified that error appears in the above-identified patent and that said Letters Patent are hereby corrected as shown below:

Column 3, line 7: "$PO_3$" should be --$P\emptyset_3$--.

Column 4, line 17: "$P_3$" should be --$P\emptyset_3$--.

Column 4, line 39, Column 5, line 9 and Column 6, line 53: "$PO_3$" should be --$P\emptyset_3$--.

Column 4, line 43: "blow" should be --blown--.

Column 8, line 24: "chlorinating" should be --chlorination--.

Signed and Sealed this

Twenty-first Day of November 1978

[SEAL]

Attest:

RUTH C. MASON
*Attesting Officer*

DONALD W. BANNER
*Commissioner of Patents and Trademarks*

UNITED STATES PATENT OFFICE
CERTIFICATE OF CORRECTION

Patent No. 4,080,398     Dated March 21, 1978

Inventor(s) Jean-Marie Basset, et al

It is certified that error appears in the above-identified patent and that said Letters Patent are hereby corrected as shown below:

Title Page, first column, lines 7-9: "[73] Assignee:

Entreprise de Recherches et D'Activites Petrolieres (ERAP), Paris, France" should be --[73] Assignee:

Societe Nationale Elf Aquitaine, Courbevoie, France --.

Signed and Sealed this

Twenty-fifth Day of September 1979

[SEAL]

Attest:

LUTRELLE F. PARKER
Attesting Officer   Acting Commissioner of Patents and Trademarks